United States Patent
Heidecke

(10) Patent No.: US 8,999,338 B2
(45) Date of Patent: Apr. 7, 2015

(54) METHOD FOR DIAGNOSIS FOR MULTIPLE SCLEROSIS INVOLVING ANTI1-RECEPTOR ANTIBODY

(75) Inventor: Harald Heidecke, Berlin (DE)

(73) Assignee: Celltrend GmbH, Luckenwalde (DE)

( * ) Notice: Subject to any disclaimer, the term of this patent is extended or adjusted under 35 U.S.C. 154(b) by 0 days.

(21) Appl. No.: 13/640,073

(22) PCT Filed: Apr. 12, 2011

(86) PCT No.: PCT/EP2011/055682
§ 371 (c)(1), (2), (4) Date: Oct. 31, 2012

(87) PCT Pub. No.: WO2011/128324
PCT Pub. Date: Oct. 20, 2011

(65) Prior Publication Data
US 2013/0066252 A1    Mar. 14, 2013

(30) Foreign Application Priority Data
Apr. 12, 2010   (EP) ..................... 10159661

(51) Int. Cl.
  A61K 39/395    (2006.01)
  G01N 33/53     (2006.01)
  G01N 33/564    (2006.01)
  A61K 38/00     (2006.01)

(52) U.S. Cl.
CPC ........ *G01N 33/564* (2013.01); *G01N 2800/285* (2013.01)

(58) Field of Classification Search
CPC combination set(s) only.
See application file for complete search history.

(56) References Cited

U.S. PATENT DOCUMENTS

2005/0014200 A1 * 1/2005 MacVicar ............... 435/7.2
2010/0098688 A1   4/2010 Schulze-Forster et al.

FOREIGN PATENT DOCUMENTS

EP       1884775 A1      2/2008
WO    WO2008015218  *   2/2008  ............ C07K 7/00

OTHER PUBLICATIONS

Wallukat et al.—Patients with preeclampsia develop agonistic auto antibodies against the angiotensin AT1 receptor, J. Clin. Investig. 103, 945-952, 1999.*
Dragun et al., Angiotensin II Type 1-Receptor Activating Antibodies in Renal-Allograft Rejection, The New England Journal of Medicine, vol. 352, 558-569, 2005.*
Liao et al., Auto antibodies against AT1-Receptor and α1-Adrenergic Receptor in Patients with Hypertension, Hypertension Res. 25, 641-646, 2002.*
Linker et al., "Role of the Renin-Angiotensin System in Autoimmune Inflammation of the CNS: Targeting the Angiotensin II Receptor as a New Therapeutic Option in Multiple Sclerosis?" European Journal of Neurology, vol. 16, No. Suppl. 3, p. 21, Oct. 1, 2009.
Lee et al., "Compounds Acting on the Renin-Angiotensin-Aldosterone System as Potential Regulators of Autoimmune Neuroinflammation," Drugs of the future, vol. 35, No. 5, pp. 393-398, (May 5, 2010).
International Search Report for PCT/EP2011/055682 Mailed Jun. 30, 2011.
Written Opinion for PCT/EP2011/055682 Completion Date Jun. 30, 2011.

* cited by examiner

*Primary Examiner* — Elly-Gerald Stoica
(74) *Attorney, Agent, or Firm* — Miles and Stockbridge

(57) ABSTRACT

The invention relates to a method for diagnosis of multiple sclerosis (MS) wherein, presence or absence of an anti-$AT_1$ receptor antibody is determined in a sample from a patient to be diagnosed and wherein, the presence of an anti-$AT_1$-receptor antibody is indicative of the disease.

11 Claims, No Drawings

METHOD FOR DIAGNOSIS FOR MULTIPLE SCLEROSIS INVOLVING ANTI1-RECEPTOR ANTIBODY

CROSS REFERENCE TO RELATED APPLICATIONS

This application is a §371 National Stage Application of PCT/EP2011/055682, filed Apr. 12, 2011, which claims priority to European Application No. 10159661.7, filed Apr. 12, 2010.

BACKGROUND OF THE INVENTION

1. Field of the Invention

Multiple sclerosis (MS, also known as disseminated sclerosis or encephalomyelitis disseminata) is a disease in which the fatty myelin sheaths around the axons of the brain arid spinal cord are damaged, leading to demyelination and scarring as well, as a broad spectrum of signs and symptoms. Disease onset usually occurs in young adults. It has a prevalence that ranges between 2 and 150 per 100,000.

1. Description of Related Art

MS affects the ability of nerve cells in the brain and spinal cord to communicate with, each other. Nerve cells communicate by sending electrical signals called action potentials down long fibers called axons, which are wrapped in an insulating substance called myelin. In MS, the body's own immune system attacks and damages the myelin. When myelin is lost, the axons can no longer effectively conduct signals. Although much is known about the mechanisms involved in the disease process, the cause remains unknown. Theories include genetics or infections. Different environmental risk factors have also been found.

Several subtypes, or patterns of progression, have been described. Subtypes use the past course of the disease in an attempt to predict the future course. They are important not only for prognosis but also for therapeutic decisions. In 1996 the United States National Multiple Sclerosis Society standardized four subtype definitions:

relapsing remitting,
secondary progressive,
primary progressive, and
progressive relapsing.

The relapsing-remitting subtype is characterized by unpredictable relapses followed by periods of months to years of relative quiet (remission) with no new signs of disease activity. Deficits suffered during attacks may either resolve or leave sequelae, the latter being more common as a function of time. This describes the initial course of 85-90% of individuals with MS. When deficits always resolve between attacks, this is sometimes referred to as benign MS, The relapsing-remitting subtype usually begins with a clinically isolated syndrome (CIS). In CIS, a patient has an attack suggestive of demyelination, but does not fulfill the criteria for multiple sclerosis. However, up to 70% of persons experiencing CIS later develop MS.

Secondary progressive MS (sometimes called "galloping MS") describes around 65% of those with an initial relapsing-remitting MS, who then begin to have progressive neurologic decline between acute attacks without any definite periods of remission. Occasional relapses and minor remissions may appear. The median time between disease onset and conversion from relapsing-remitting to secondary progressive MS is 19 years.

The primary progressive subtype describes the approximately 10-15% of individuals who never have remission after their initial MS symptoms. It is characterized by progression of disability from onset, with no, or only occasional and minor, remissions and improvements. The age of onset for the primary progressive subtype is later than for the relapsing-remitting, but similar to mean age of progression between the relapsing-remitting and the secondary progressive. In both cases it is around 40 years of age.

Progressive relapsing MS describes those individuals who, from onset, have a steady neurologic decline but also suffer clear superimposed attacks.

Cases with non-standard behavior have also been described. Sometimes referred to as borderline forms of multiple sclerosis, these include Devic's disease. Balo concentric sclerosis, Schilder's diffuse sclerosis and Marburg multiple sclerosis.

Multiple sclerosis can be difficult to diagnose since its signs and symptoms may be similar to other medical problems. Medical organizations have created diagnostic criteria to ease and standardize the diagnostic process for practicing physicians, especially in the first stages of the disease. Historically, the Schumacher and Poser criteria were both popular (Poser et al. (2004), "Diagnostic criteria for multiple sclerosis: an historical review". Clin Neurol Neurosurg 106 (3): 147-58). Currently, the McDonald criteria focus on a demonstration with clinical, laboratory and radiologic data of the dissemination of MS lesions in time and space (Polman et al. (2005). "Diagnostic criteria for multiple sclerosis: 2005 revisions to the "McDonald Criteria"", Ann. Neurol 58 (6): 840-6).

Since no known test is perfectly specific to MS, only biopsies or post-mortem, examinations can yield an absolutely certain diagnosis.

Thus, there is a need for a diagnostic tool for diagnosing multiple sclerosis. Further, there is a need for a medicament for the treatment of sclerosis.

The present invention addresses the need for a diagnostic tool for the above-mentioned family of diseases. The present invention further addresses the need for a medicament for treating the above-mentioned diseases.

SUMMARY

The present invention relates to a method for diagnosis of multiple sclerosis, wherein presence or absence of an anti-$AT_1$-receptor antibody is determined in a sample from a patient to be diagnosed and wherein, the presence of an Anti-$AT_1$-receptor antibody is indicative of the disease.

The inventors have found that 25% of patients with multiple sclerosis ate positive for the presence of an anti-$AT_1$-antibody.

Determination was performed in blind test fashion. All patients with multiple sclerosis displayed severe complications and were difficult to treat with standard methods. There was a clear correlation between the presence of the anti-$AT_1$ antibody and the disease.

In a preferred embodiment of the invention the determination of presence or absence of an anti-$AT_1$-receptor antibody is done by detecting one or more of the antibodies selected from the group of IgA-antibody IgG-antibody and IgM-antibody and more in particular an IgG1, IgG2, IgG3 and IgG4 antibody.

In one embodiment of the invention me invention relates to an immunoassay. There are numerous ways of performing an immunoassay. In a preferred embodiment of the invention, the immunoassay is a luciferase assay and/or an ELISA.

The invention further relates to the use of an $AT_1$-receptor-peptide or a functional analog thereof for the diagnosis of a disease and is selected from, the group of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis and Marburg multiple sclerosis.

The invention relates to a research and/or diagnostic kit tor the diagnosis of multiple sclerosis, wherein the kit comprises an $AT_1$-receptor-peptide or a functional analog thereof.

In a further embodiment the invention relates to the use of an inhibitor of an anti-$AT_1$-receptor-antibody or an inhibitor of an $AT_1$-receptor for the production of a medicament for treating MS.

The invention also relates to a kit for the diagnosis of multiple sclerosis, wherein the kit comprises an $AT_1$ receptor peptide or a functional analogue thereof.

DETAILED DESCRIPTION OF A PREFFERED EMBODIMENT

The inventors have found that certain diseases may be diagnosed by detecting the presence or absence of an anti-$AT_1$-receptor antibody in a sample from a patient to be diagnosed. In fact, the inventors have found that 25% of patients which have multiple sclerosis are positive for the anti-$AT_1$-antibody.

Thus, the present invention relates to a method tor diagnosis of a disease, wherein presence or absence of an anti-$AT_1$-receptor antibody is determined in a sample from a patient to be diagnosed.

It has been possible to demonstrate that there is a relationship between the presence of said anti-$AT_1$-receptor antibody and the likelihood of multiple sclerosis. It has been demonstrated that the presence of the anti-$AT_1$-receptor antibody gives rise to multiple sclerosis. Further, the presence of an anti-$AT_1$-receptor antibody is diagnostic for multiple sclerosis.

In connection with the present invention, a number of general terms will be used as follows:

The "$AT_1$-receptor" may be present in its natural cellular environment and can be used together with the material associated with the receptor in its natural state as well as in isolated form with respect to its primary, secondary and tertiary structures, the $AT_1$-receptor is well known to those skilled in the art. Based on the weight of the whole receptor in the preparation to be used according to the invention, the isolated receptor should account for at least 0.5%, preferably at least 5% more preferably at least 25%, and in a particular preferred embodiment at least 50%. the receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the $AT_1$-receptor can be used. Similarly, an $AT_1$-receptor produced by means of recombinant techniques, which receptor includes amino acid modifications, such as inversions, deletions, insertions, additions etc. can be used according to the invention provided that this part of the essential function of the $AT_1$-receptor is present, namely the capability of binding antibodies. The $AT_1$-receptor being used may also comprise exceptional amino acids and/or modifications of such as alkylation, oxidation, thiol-modification, denaturation, oligomerization and the like. The receptor can also be synthesized by chemical means. According to the invention the $AT_1$-receptor particularly can be a protein and/or peptide or a fusion protein, which in addition to other proteins, peptides or fragments thereof includes the $AT_1$-receptor as a whole or in part. Using conventional methods, peptides or polypeptides of the $AT_1$-receptor which have functionally analogs, analogous properties can be determined by those skilled in the art. For example such polypeptides or peptides have 50-60%, 70% or 80%, preferably 90%, more preferably 95%, and most preferably 98% homology to peptides identified as $AT_1$-receptor, and said homology can be determined, e.g. by means of Smith-Waterman homology search algorithm, using the MPFRCH Programme (Oxford Molecular), for example.

The term "peptide" of an $AT_1$-receptor used in the present invention, comprises also molecules differing from the original, sequence by deletion(s), insertion(s), substitution(s) and/or other modifications well known in the prior art and/or comprising a fragment of the original amino acid molecule, the $AT_1$-receptor still exhibiting the properties mentioned above. Also included are allele variants and modifications. Methods of producing the above changes in the amino acid sequence are well known to those skilled in the art and have been described in the standard textbooks of molecular biology, e.g. Sambrook et al. Supra. Those skilled in the art will also be able to determine whether an $AT_1$-receptor, thus, modified still has the properties mentioned above. Possible $AT_1$-receptor peptides used according to the invention can be, e.g. AVHYQSN (SEQ ID NO. 1); SHFYQTR (SEQ ID NO. 2) and/or GYYFDTN (SEQ ID NO. 3).

In the present specification all of the above illustrated modifications of the $AT_1$-receptor will be referred to as "functionally analogous peptides or proteins" in brief.

"Sample" in the meaning of the invention can be all biological tissues and fluids such as blood, lymph, urine, cerebral fluid. The sample is collected from the patient and subjected to the diagnosis according to the invention.

The "anti-$AT_1$-receptor antibody" in the meaning of the invention, which is to be detected, binds the $AT_1$-receptor in a specific fashion. The antibody can also be modified (e.g. oligomeric, reduced, oxidized and labeled antibodies). The term anti-$AT_1$-receptor antibody as used herein comprises both intact molecules and also anti-$AT_1$-receptor antibody fragments such as Fab, F(ab')$_2$ and Fv capable of binding specific epitope determinance of the $AT_1$-receptor. In these fragments the anti-$AT_1$-receptor antibody(ies) capability of selectively binding its antigen or receptor is retained in part, the fragments being defined as follows: (1) Fab, the fragment which contains a monovalent antigen-binding fragment of an antibody molecule, can be generated by cleavage of a whole antibody using the enzyme papaine, thereby obtaining an intact light chain and part of a heavy chain; (2) the Fab fragment of an antibody molecule can be produced by treatment of a whole antibody with pepsin and subsequent reduction, thereby obtaining an intact light chain and part of a heavy chain, two Fab fragments per antibody molecule are obtained: (3) F(ab')$_2$ the fragment of the antibody which can be obtained by treatment of a whole antibody with, the enzyme pepsin without subsequent reduction, F(ab')$_2$ is a dimer comprised of two Fab fragments held together by two disulfide bonds; (4) Fv defined as fragment modified by genetic engineering which includes the variable region of the light chain and the variable region of the heavy chain is expressed in the form of two chains; and (5) single-chain antibody (SCA) defined as a molecule modified by genetic engineering, which includes the variable region of the light chain and the variable region of the heavy chain, linked by a suitable polypeptide linker to perform, a genetically fused single-chain molecule.

The term "epitope" as used in the present invention represents any antigen determinant on the $AT_1$-receptor. Epitope determinance normally consists of chemically active surface groups of molecules such, as amino acids or sugar-side chains and normally has specific features of the free dimensional structure as well as specific chart properties.

The anti-$AT_1$-receptor antibody binds specifically to the $AT_1$-receptor or in doing so shows specific immuno reactivity when, the anti-$AT_1$-receptor antibody assumes its function in a binding reaction in the presence of a heterogeneous population of $AT_1$-receptors or fragments thereof, thereby allowing a conclusion whether the $AT_1$-receptor or another biological structure is present. Under the present conditions of an immunoassay, the above-mentioned anti-$AT_1$-receptor antibodies will preferably bind to a specific portion of the $AT_1$-receptor, while no significant binding to other proteins present in the sample will take place.

"Patients" in the meaning of the invention are understood to be all persons, animals, plants or microorganisms, irrespective whether or not they exhibit pathological changes. In the meaning of the invention, any sample collected from cells, tissues, organs, organisms or the like can be a sample of a patient to be diagnosed. In a preferred embodiment the patient according to the invention is a human. In a further preferred embodiment of the invention the patient is a human suspected to have a disease selected from the group of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis and Marburg multiple sclerosis.

According to the invention the disease is selected from the group consisting of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis and Marburg multiple sclerosis.

In a preferred embodiment of the invention the determination of the presence or the absence of an anti-$AT_1$-receptor antibody is done by detecting one or more of the antibodies selected from the group of IgA-antibody, IgG-antibody and IgM-antibody.

Human antibodies can be divided into five classes of immunoglobulins. Class A immunoglobulin (IgA) exists in form which is dissolved in blood as well as in secretory variant. IgA comprises two basic classes. Secretory IgA consist of two immunoglobulin basic molecules, together with a J-chain and a secretory component. More specifically, IgA molecules is prevalent in body secretions.

Class IgG immunoglobulins represent the major part among the immunoglobulins. The antibodies of the secondary immune response taking place upon contact of the immune system of a particular antigen largely belong to the IgG class.

In a particularly preferred embodiment of the invention, the anti-$AT_1$-receptor antibody is selected from the group of IgG1, IgG2, IgG3 and IgG4.

An "immune reaction" in the meaning of the invention is a specific interaction between the $AT_1$-receptor or peptides or proteins of analogous function and anti-$AT_1$-receptor antibodies. The immune reaction can be detected using various immunoassays.

"Immunoassays" in the meaning of the invention are assays utilizing the specific interaction between the $AT_1$-receptor and peptides or proteins of analogous function and the anti-$AT_1$-receptor antibody, in order to detect the presence or determine the concentration of the anti-$AT_1$-receptor antibodies. For example, the detection and quantification of the anti-$AT_1$-receptor antibody can be performed with the aid of said peptides or proteins an analogous function, e.g. by immunoprecipitation or immunoblotting. For example, immunoassays in the meaning of the invention can be subdivided into the following steps: (1) anti-$AT_1$-receptor antibody/$AT_1$-receptor reaction, (2) if required separation of the anti-$AT_1$-receptor antibody complex from other components of the reaction mixture especially from non-bound anti-$AT_1$-receptor antibodies an $AT_1$-receptor and (3) measuring the response. As for the anti-$AT_1$-receptor antibody/$AT_1$-receptor reaction various configurations of passable, e.g. (a) precipitation of one reaction with an access of the other or (b) competition between known quantities of anti-$AT_1$-receptor antibody or $AT_1$-receptor and the material to be investigated.

For example, an assay for anti-$AT_1$-receptor antibodies can be performed by a) using access $AT_1$-receptors/peptides or proteins of analogous function or b) competition between a labeled anti-$AT_1$-receptor antibody of known amount and non-labeled antibody of unknown amount for a defined quantity of $AT_1$-receptor or peptides of proteins of analogous function.

The $AT_1$-receptor can be immobilized on a solid support. To allow separation of the anti-$AT_1$-receptor antibody/$AT_1$-receptor complex. For example, the solid support material, can be nitrocellulose, polyvinylchloride or polystyrene, e.g. the well of a microtiter plate. The immunoassay may take place in a micro fluidic environment. To measure the anti-$AT_1$-receptor antibody/$AT_1$-receptor interaction, it is possible to use labeled anti-$AT_1$-receptor antibodies, labeled $AT_1$-receptors or secondary reagents, for example. The $AT_1$-receptor can be labeled radioactively or with enzymes or with fluorescent compounds, for example, irrespective of the label that is used, the response of the anti-$AT_1$ receptor antibody/$AT_1$-receptor interaction can be enhanced by utilizing the affinity of the proteins avidine or streptavidine for biotin. The immunoassays used according to the invention can be; (1) immunoassays using radioactive label: (a) radioimmunoassay with competitive binding (RIA) and (b) immunoradiometric assay (IRMA); (2) immunoassays using an enzyme label: (a) enzyme immunoassays (EIA) and (b) enzyme-linked immunosorbent assays (ELISA); (3) immunoassays using a combination of radioisotope and enzyme labels (ultrasensitive enzyme radio immunoassay) (USERIA). Further, the immunoassay according to the invention may be a fluorescent immunoassay, a chemiluminescent assay, an agglutination assay, a nephelometric assay, a turbidimetric assay, a Western Blot, a competitive immunoassay, a non-competitive immunoassay, a homogenous immunoassay, a heterogenous immunoassay, a reporter-assay, e.g. a luciferase assay.

In a preferred embodiment of the invention the immunoassay is an ELISA.

The invention also relates to the use of an $AT_1$-receptor-peptide or a functional analog thereof for the diagnosis of a disease selected of the group of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease. Bale concentric sclerosis, Schilder's diffuse sclerosis and Marburg multiple sclerosis.

The invention further relates to a research and/or diagnostic kit for the use in the diagnosis of a disease selected from the group of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis and Marburg multiple sclerosis, wherein the kit comprises an $AT_1$-receptor peptide or a functional analog thereof.

In a preferred embodiment the research and/or diagnostic kit comprises an $AT_1$-receptor-peptide or a functional analog thereof.

The immunological test kit according to the invention comprises the $AT_1$-receptor or a functional analog thereof or peptides or proteins of analogous function per se. The test kit of the invention comprises at least one complete $AT_1$-receptor or functionally analogous peptides or proteins of said receptor, optionally bound to a solid phase. Furthermore, the test kit may also comprise buffers, specific conjugate together with an enzyme, wash solution, substrate solution to detect the immune reaction and/or a quenching solution. Using these substances a person skilled in the art will be able to perform, e.g. an ELISA to detect the anti-$AT_1$-receptor antibodies. The buffers, specific conjugate plus enzyme, wash solution, substrate solution to detect immune reaction and quenching solution are well known to those skilled in the art. For example, it would be sufficient to have the test comprise a freeze-dried $AT_1$-receptor or peptides or proteins of $AT_1$-receptor analogous function and to add the buffers and other solutions immediately prior to testing the biological material. However, it is also possible to provide the test kit with the $AT_1$-receptor or its functionally analogous peptides of proteins bound to a solid phase. To detect the anti-$AT_1$-receptor antibodies the specific conjugate, wash solution, substrate solution and quenching solution, which can be components of the test kit, have to be added according to a mode well known to those skilled in the art.

In another advantageous embodiment of the invention, it is envisioned that the test kit is a test strip comprising the $AT_1$-receptor, or its functionally analogous peptides or proteins immobilized on a solid phase. For example, the test strip can be immersed in serum, or other patient samples and incubated. Using a specific biochemical reaction on the test strip after formation of the $AT_1$-receptor/anti-$AT_1$-receptor antibody complex, a specific color reaction, can be triggered by means of which the anti-$AT_1$-receptor antibody can be detected.

The test system, of the invention permits quantification of the anti-$AT_1$-receptor antibodies directly in a sample, e.g. in plasma of patients. The detection method according to the invention is time saving and cost effected. Large amounts of the samples can be tested and, owing to the low amount of the equipment required, routine laboratories can be used.

The invention also relates to an inhibitor of an anti-$AT_1$-receptor antibody and an inhibitor of an $AT_1$-receptor for the production of a medicament for the treatment of a disease selected from the group consisting of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease. Bale concentric sclerosis, Schilder's diffuse sclerosis and Marburg multiple sclerosis.

The term "inhibitor" refers to an agent that binds to the receptor hut does not provoke the normal biological response. For example, an inhibitor may he any molecule which, when bound to an $AT_1$-receptor, decreases the activity of or reduces the expression levels of the $AT_1$-receptor.

In a preferred embodiment the inhibitor of the $AT_1$-receptor or the anti-$AT_1$-receptor antibody is selected from the group of
(i) losartan (1-((2'-(2H-tetrazol-5-yl)biphenyl-4-yl)methyl)-2-butyl-4-chloro-1H-imidazol-5-yl)methanol) an inhibitor of the $AT_1$-receptor,
(ii) candesartan (3-((2'-(2H-tetrazol-5-yl)biphenyl-4-yl)methyl)-2-ethoxy-3H-benzo[d]imidazole-4-carboxylic acid) an inhibitor of the $AT_1$-receptor,
(iii) eprosartan (4-[[2-butyl-5-(2-carboxy-3-thiophen-2-yl-prop-1-enyl)-imidazol-1-yl]methyl]benzoic acid) an inhibitor of the $AT_1$-receptor,
(iv) irbesartan (2-butyl-3-[p-(o-1H-tetrazol-5-ylphenyl)benzyl]-1,3-diazaspiro[4.4]non-1-en-4-one) an inhibitor of the $AT_1$-receptor,
(v) olmesartan an inhibitor of the $AT_1$-receptor,
(vi) telmisartan (2-[4-[[4-methyl-6-(1-methylbenzoimidazol-2yl)-2-propyl-benzoimidazol-1-yl]methyl]phenyl]benzoic acid) an inhibitor of the $AT_1$-receptor,
(vii) valsartan an inhibitor of the $AT_1$-receptor,
(viii) an anti-sense molecule directed against the $AT_1$-receptor or the anti-$AT_1$-receptor antibody,
(ix) antibodies against the $AT_1$-receptor,
(x) antibodies against the anti-$AT_1$-receptor antibody, and
(xi) a nucleic add molecule that results in silencing $AT_1$-receptor activity through, RNAi such as dsRNA.

Plasmapheresis (from the Greek plasma, something molded, and apheresis, taking away) is the removal of (components of) blood plasma from the circulation. It is used as a therapy in particular diseases, and it is also a method by which blood donors donate only plasma, with remaining red cells and platelets returned to their circulatory systems, allowing up to twice weekly plasma donations.

An important use of plasmapheresis is in the therapy of multiple sclerosis, where the symptoms are so catastrophic that medical therapy is insufficient in controlling the symptoms. Plasmapheresis clears antibodies from circulation.

Other uses are the removal of Wood proteins where these are overly abundant and cause hyperviscosity syndrome.

In one embodiment of the invention the invention relates to a method for the removal of anti-$AT_1$-receptor antibody, wherein in a first step the presence or absence of an anti-$AT_1$ receptor antibody is determined in a blood, sample from a patient to be diagnosed for a multiple sclerosis selected from, the group of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis and Marburg multiple sclerosis, wherein upon determining the presence of an anti-$AT_1$-receptor antibody the blood of the patient is subjected to a plasmapheresis. The invention preferably relates to an in vitro test. Also the invention relates to monitoring the level of $AT_1$ receptor antibodies in patients that have MS or are suspected to have MS. Tissues to be analyzed include body fluids such as blood serum, or other fluids such as urine or saliva. They include other tissues such as liver, heart, lung and other organs. Preferably the level of $AT_1$-receptor antibodies is determined in blood, whole blood or sera. Most preferably serum is used.

Plasmapheresis may be performed multiple times. In a preferred embodiment it is performed in intervals of 4 weeks until the titer of the anti-$AT_1$-antibody is below detection level.

The invention also relates to a kit for the diagnosis of multiple sclerosis, wherein the kit comprises an $AT_1$ receptor peptide or a functional analogue thereof.

As used herein, a "kit" is a packaged combination optionally including instructions for use of the combination and/or other reactions and components for such use.

Angiotensin II (AngII) is the major effector molecule of the renin-angiotensin system. It exerts its various actions on the cardiovascular and renal system, mainly via the AngII type 1 receptor ($AT_1$-receptor). Moreover, Ang II was shown to be a potent pro-inflammatory mediator and recent data highlight the role of the HAS in animal models of multiple sclerosis (MS). In particular, activating antibodies to the $AT_1$-receptor may play a role for the outcome of T cell mediated diseases like renal allograft rejection.

After obtaining informed consent, sera from patients with MS and respective controls were analysed for the presence of activating anti-$AT_1$-receptor antibodies by a newly developed cellular ELISA based on cell lines transfected with the $AT_1$-receptor. MS patients were characterized for their disease course, treatment, and disease activity based on relapses, EDSS progression and MRI activity as defined by gadolinium enhancement of lesions.

From 48 MS patients, 67% presented with a relapsing disease course. In the sera from these patients, significant reactivities towards the $AT_1$-receptor are present in 25% of subjects, Anti-$AT_1$-receptor antibody titres were significantly higher in the subgroup of MS patients with recent disease activity (mean±SEM: 25.6±3.9 bpm in patients with recent relapses or contrast enhancing lesions vs. 12±1.5 in patients with relapsing remitting MS without disease activity; $p<0.001$). The presence of anti-$AT_1$-receptor antibodies was not associated with EDSS, duration of disease, or pre-existing therapies.

Anti-$AT_1$-receptor antibodies serve as a biomarker for disease activity in MS with relapses. The detection of these antibodies identifies MS patients at risk who may benefit from a therapeutic modulation of the renin angiotensin system.

The invention claimed is:

1. A method for complementing the diagnosis of multiple sclerosis in a patient suspected to have multiple sclerosis based on diagnostic criteria comprising obtaining a sample from the patient and performing an immunoassay on the sample to determine the presence or absence of an anti-$AT_1$ receptor antibody in the sample, wherein the presence of an anti-$AT_1$-receptor antibody is indicative of multiple sclerosis, and wherein the patient is human.

2. The method according to claim 1, wherein said multiple sclerosis is selected from the group consisting of multiple sclerosis, relapsing remitting multiple sclerosis, secondary progressive multiple sclerosis, primary progressive multiple sclerosis, progressive relapsing multiple sclerosis, and borderline forms of multiple sclerosis including Devic's disease, Balo concentric sclerosis, Schilder's diffuse sclerosis, and Marburg multiple sclerosis.

3. The method according to claim 1, wherein the determination of presence or absence of an anti-$AT_1$ receptor antibody is done by detecting at least one of the antibodies selected from the group consisting of IgA-antibody, IgG-antibody, and IgM-antibody.

4. The method according to claim 3, wherein the IgG-antibody is detected and is selected from the group consisting of IgG1, IgG2, IgG3, and IgG4.

5. The method according to claim 1, wherein the immunoassay is selected from the group consisting of immunoprecipitation, enzyme immunoassay (EIA), radioimmunoassay (RIA), fluorescent immunoassay, a chemiluminescent assay, an agglutination assay, nephelometric assay, turbidimetric assay, a Western blot, a competitive immunoassay, a noncompetitive immunoassay, a homogeneous immunoassay, a heterogeneous immunoassay, a bioassay, and a reporter-assay optionally comprising a Luciferase-Assay.

6. The method according to claim 1, wherein said immunoassay is an ELISA.

7. The method according to claim 1, wherein said multiple sclerosis is multiple sclerosis with relapses.

8. The method according to claim 1, wherein said anti-$AT_1$-receptor antibodies are a biomarker for disease activity in multiple sclerosis with relapses.

9. A method for complementing the diagnosis of multiple sclerosis in a patient suspected to have multiple sclerosis based on diagnostic criteria comprising obtaining serum from the patient and performing a cellular ELISA on the serum to determine the presence or absence of an anti-$AT_1$ receptor antibody in the serum, wherein the presence of an anti-$AT_1$-receptor antibody is indicative of multiple sclerosis, and wherein the patient is human.

10. The method according to claim 1, wherein an $AT_1$ receptor peptide is used to determine the presence or absence of an anti-$AT_1$ receptor antibody in the sample.

11. The method according to claim 1, wherein said method comprises utilizing an immunological test kit, wherein said kit comprises an $AT_1$-receptor peptide.

* * * * *

UNITED STATES PATENT AND TRADEMARK OFFICE
CERTIFICATE OF CORRECTION

PATENT NO. : 8,999,338 B2  
APPLICATION NO. : 13/640073  
DATED : April 7, 2015  
INVENTOR(S) : Harald Heidecke Page 1 of 1

It is certified that error appears in the above-identified patent and that said Letters Patent is hereby corrected as shown below:

On The Title Page, Item (54) Title should read --METHOD FOR DIAGNOSIS OF MULTIPLE SCLEROSIS INVOLVING ANTI-AT1-RECEPTOR ANTIBODY--.

Signed and Sealed this
Fifteenth Day of December, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 7
<212> TYPE: PRT
<213> ORGANISM: Homo sapiens

<400> SEQUENCE: 1

Ala Val His Tyr Gln Ser Asn
1               5

<210> SEQ ID NO 2
<211> LENGTH: 7
<212> TYPE: PRT
<213> ORGANISM: Homo sapiens

<400> SEQUENCE: 2

Ser His Phe Tyr Gln Thr Arg
1               5

<210> SEQ ID NO 3
<211> LENGTH: 7
<212> TYPE: PRT
<213> ORGANISM: Homo sapiens

<400> SEQUENCE: 3

Gly Tyr Tyr Phe Asp Thr Asn
1               5
```